United States Patent [19]
Spielmann et al.

[11] Patent Number: 5,181,609
[45] Date of Patent: Jan. 26, 1993

[54] DISPOSABLE RECEPTOR FOR SURGICAL SHARPS

[76] Inventors: Susan A. Spielmann; Thomas G. Spielmann, both of Rte. 1 Box 67 Cole La., Aurora, Ind. 47001

[21] Appl. No.: 865,959

[22] Filed: Apr. 9, 1992

[51] Int. Cl.⁵ .............................................. B65D 85/24
[52] U.S. Cl. ................................... 206/370; 206/366; 206/818
[58] Field of Search ....................... 206/370, 366, 818

[56] References Cited

U.S. PATENT DOCUMENTS

| | | | |
|---|---|---|---|
| 4,013,109 | 3/1977 | Sandel | 206/818 |
| 4,344,532 | 8/1982 | Eldridge, Jr. et al. | 206/370 |
| 4,373,629 | 2/1983 | Ulin et al. | 206/370 X |
| 4,736,844 | 4/1988 | Scott et al. | |
| 4,886,165 | 12/1989 | Annett | |
| 4,936,449 | 6/1990 | Conard et al. | |
| 5,005,590 | 4/1991 | Eldridge, Jr. et al. | 206/370 X |
| 5,024,326 | 6/1991 | Sandel et al. | |

Primary Examiner—William I. Price
Attorney, Agent, or Firm—Frost & Jacobs

[57] ABSTRACT

A disposable device for receiving and holding sharp implements such as surgical sharps or the like includes a top member connected in spaced apart relationship to a bottom member and defining a substantially enclosed receiving area therebetween. The top member has an outer magnetic surface for receiving and retaining various sharp implements, while at least a portion of the receiving area also includes a magnetic surface adjacent the bottom member. A portion of the receiving area also houses a foam block or similar material for frictionally receiving and retaining additional sharp implements such as needles or the like, and the top member can be hinged for selectively providing unencumbered visual access to the contents of the normally enclosed receiving area. In the surgical context, the disposable device provides optimum positive retention and visual access for substantially all commonly utilized surgical sharps, with the enclosed receiving area providing a convenient and protected area for temporary storage of scalpels and the like which must be reused during any particular procedure.

18 Claims, 1 Drawing Sheet

U.S. Patent  Jan. 26, 1993  5,181,609
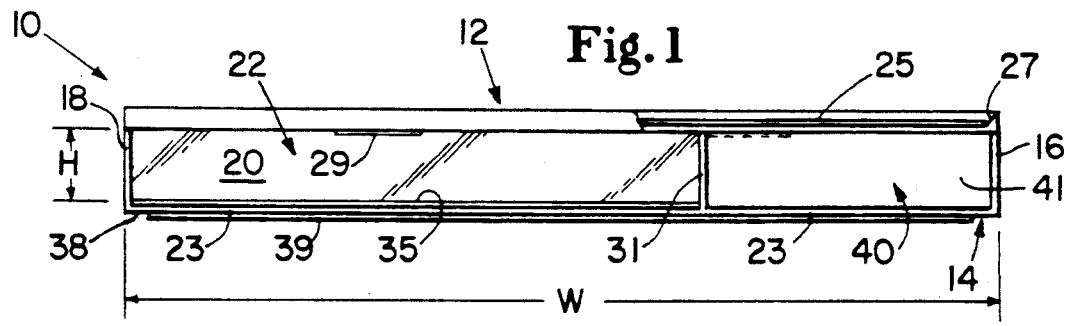
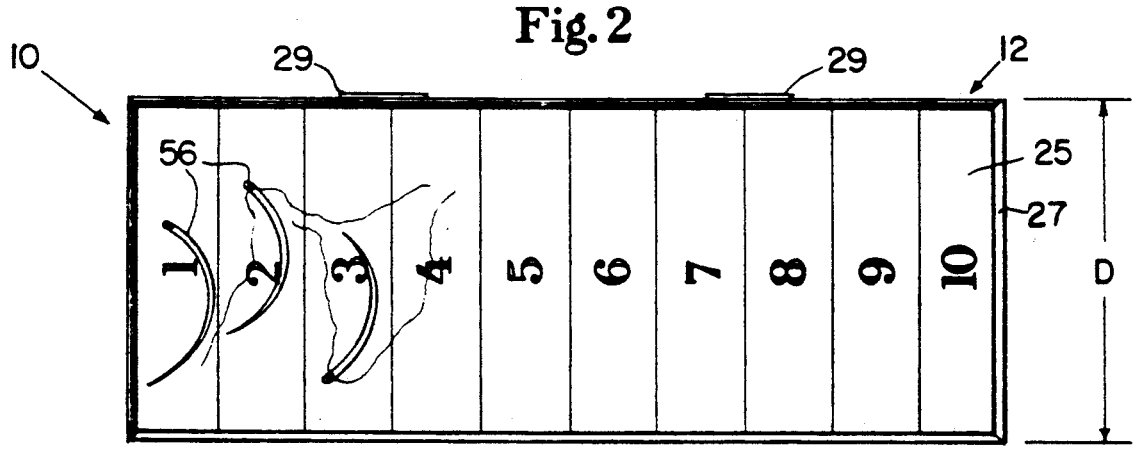
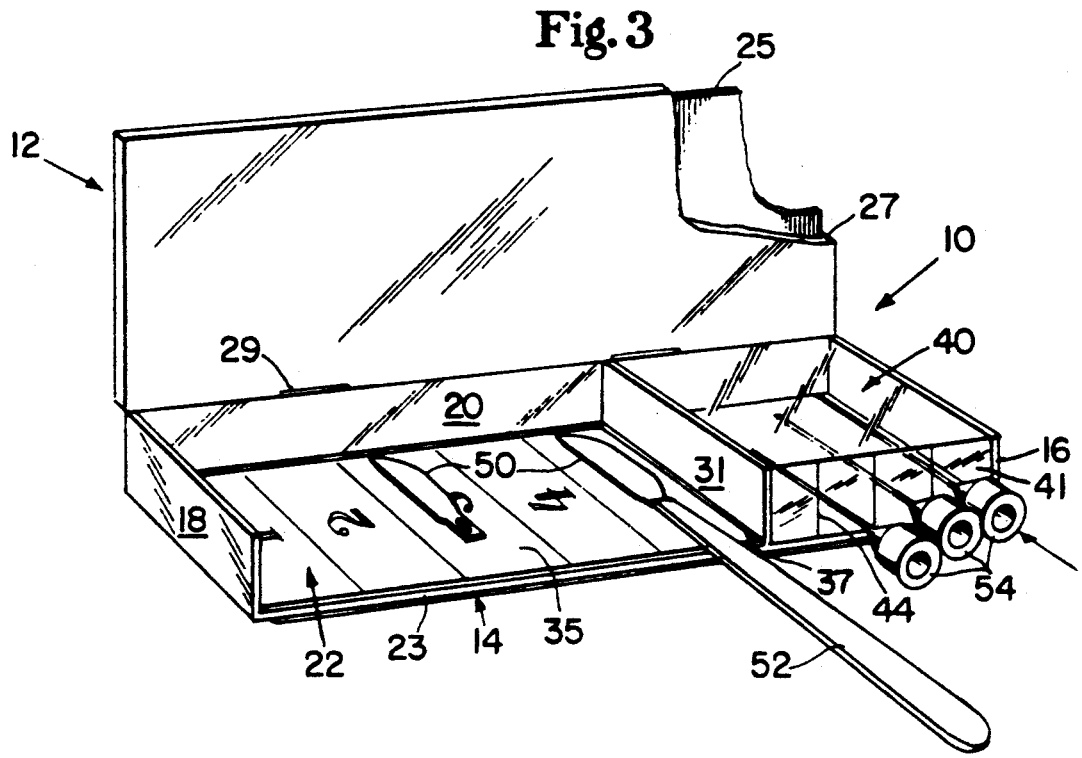

DISPOSABLE RECEPTOR FOR SURGICAL SHARPS

TECHNICAL FIELD

This invention relates to devices for receiving used disposable sharp instruments such as scalpels, suture needles and other needles used in surgical procedures and the like. And, more particularly, to a simple disposable device which receives and maintains surgical sharps in a manner which not only minimizes chances for contact and/or injury of personnel and staff in the operating room, but further facilitates keeping track of such instruments during and following such procedures.

BACKGROUND ART

In a variety of procedures utilizing relatively small tools, instruments, and/or other implements, it is often desirable or necessary to provide a container or other medium for keeping track of and temporarily storing such various devices. In particular, in surgical procedures it is extremely critical to constantly maintain an accurate count and accounting for the various medical and surgical implements utilized during any particular procedure. In this regard, failure to maintain such control over scalpels, scalpel blades, suture needles, injection needles and other surgical sharps can be hazardous to both patient and surgical staff alike.

During various surgical procedures, it is often also necessary for the surgeon to use several different scalpels and/or to utilize other surgical sharps such as hypodermic needles and the like repeatedly at intermittent times throughout the procedure. As a consequence, surgical sharps must often be temporarily stored (e.g., on an instrument platform or the like) during the procedure for quick access as needed. As can be imagined, exposed scalpels and the like can pose significant health and safety threats to persons in the operating room, and protection from such instruments is important for reducing the risk of unnecessary cuts, scratches, and/or infection.

Recognizing these critical needs, a variety of devices and containers have been devised in an attempt to conveniently and reliably contain surgical sharps. For example, U.S. Pat. No. 4,886,165, which issued to L. Annett, discloses a hinged container having a bottom and cover joined by a common hinge. The Annett container is to be utilized in a folded-open condition, and the common hinge can be split apart to enable separation of the two pieces for separate use. The bottom portion of the container includes a magnetic insert to retain magnetic surgical articles, or may be provided with a cushioned pad to help retain small surgical articles. This magnetic insert or cushioned pad may also be provided with indicia for facilitating an account of the surgical implements contained. This device, however, must be maintained in its open condition during use, as temporary storage of surgical implements is only possible while the device is maintained in open condition. As a result, the surgical implements are still accessible to inadvertent contact with operating room personnel and the like, and the instruments must either be removed from the container, or the container left in an open condition, for movement of the container and/or disposal procedures.

Another device for retaining and disposing of surgical sharps is set illustrated in U.S. Pat. No. 4,936,449, which issued to D. Conard et al. The Conard et al. device comprises a container and lid arrangement designed to lock together in closed condition to reduce the likelihood of removal of inserted sharps. The container portion of the device may also include a block of styrofoam for receiving the surgical sharps prior to closure by the locking lid. The use of the detachable Conard lid to carry and hold various medical equipment, however, requires multiple handling of the surgical implements in order to enable the closure of the device following use. Moreover, this device does not provide for convenient receiving and/or containment of smaller surgical sharps such as suture needles or discarded scalpel knife blades.

U.S. Pat. No. 4,736,844, which issued to S. Scott et al., discloses a multi-compartment container which includes one shallow compartment having a pair of spaced foam strips for receiving needles and the like, as well as a hinged lid attached thereto and having an adhesive layer on its inner surface for receiving suture needles. An additional closed compartment is also provided for the insertion of used scalpel blades, wherein the upper face of this closed compartment is transparent to enable the contents of the closed compartment to be inspected. Again, the Scott container must be maintained in an open condition for use, and does not provide for relatively enclosed temporary storage of surgical sharps during the operating procedures. Additionally, often in the relatively compressed time periods allotted for surgical procedures, careful insertion of used needles into the foam strips or the like is not practical under the circumstances, and reuse of instruments inadvertently laid upon the adhesive layer may be difficult. This device must also be folded into a closed condition, or carefully moved in its open condition for disposal procedures. Loose needles and the like can require additional handling for proper disposal.

Devices similar to the Scott et al. container have also been available with one or more of the adjacent compartments includes a magnetic surface, similar to that described above with respect to the Annett patent. Again, these fold-open type containers do not provide a substantially closed receiving area for temporary storage of surgical sharps, and must either be folded closed after use or carefully moved in an open condition following use. As will be understood, additional handling of surgical sharps, which often have blood and/or other foreign bodily fluids on their surfaces, is clearly not desirable under any circumstance.

Yet another device designed for holding medical instruments and disposing of surgical sharps is shown in U.S. Pat. No. 5,024,326, which issued to D. Sandel et al. Particularly, the Sandel patent shows and describes a medical instrument holder which must also be used in a folded-open condition. The device comprises a pair of plastic body halves, with one half including an inclined medical instrument rest member which enables temporary storage of instruments in an outwardly angled orientation. A cushion of foam is provided to receive the tips of sharp instruments positioned on the rest, and a magnetic surface is provided within the lid portion of the container body to hold discarded surgical sharps. Again, this device must be closed for disposal, or discarded in an open condition, which will generally require removal of the instruments and additional handling of non-sterile sharps.

As can be seen, while a great number of attempts have been implemented to address the continuing problems of carefully accounting for the various medical instruments and sharp devices utilized in surgical procedures, heretofore there has not been available a single device which can effectively receive and retain substantially all kinds of surgical sharps in a reliable and simple manner, and which provides for the temporary storage of sharp instruments without requiring opening or closing of the container or multiple handling of the contaminated instruments. Particularly, no single device could provide reliable one-time handling of essentially all of the various surgical sharps commonly utilized in surgical procedures while providing for convenient accounting of all such instruments in an organized manner and minimizing handling requirements and facilitating counts and visual accounting of the sharps.

DISCLOSURE OF THE INVENTION

It is an object of this invention to obviate the above-described problems and shortcomings of the containers and other devices heretofore available for receiving and disposing of surgical sharps.

It is another object of the present invention to provide an improved surgical sharp receptor which is simple in construction and simple to use.

It is yet another object of the present invention to provide a single disposable container for surgical scalpels, suture needles, hypodermic needles and the like which provides reliable positive reception and maintenance of discarded surgical sharps, and further provides for temporary storage of surgical sharps in a substantially enclosed receiving area.

It is also an object of the present invention to provide a relatively simple surgical sharp container which is designed to receive the various different kinds of surgical sharps commonly utilized in the operating room and to actively retain those sharps to facilitate accounting therefor and to minimize the chances of inadvertent contact with person in the operating room.

It is yet another object of the present invention to provide an improved and simplified receptor for surgical sharps designed to provide maximum positive control of and accounting for surgical sharps in a simple, and easy to use container which also provides a substantially closed temporary storage area for sharp instruments which may require multiple uses from time to time during the operation.

In accordance with one aspect of the present invention, there is provided a disposable device or receptor for receiving and retaining sharp implements such as surgical scalpels, hypodermic needles, suture needles, and the like, and including a top member connected in spaced apart relationship with a bottom member by a plurality of adjacent peripheral walls. In a preferred embodiment, the top and bottom members are spaced apart in substantially parallel relationship, and, together with the peripheral walls, define a substantially enclosed receiving area therebetween. The top member includes an outer magnetic surface, and at least a portion of the receiving area includes a similar magnetic surface adjacent the bottom member. In a preferred embodiment, a block of foamed material is situated between the top and bottom members within a portion of the enclosed receiving area for releasably receiving and retaining surgical sharps such as hypodermic needles. Also in a preferred embodiment, at least a portion of the top member is hingedly attached for providing selective unencumbered visual access to the normally enclosed receiving area. The top member is normally held in its closed position to maintain the receiving area in a substantially enclosed condition. During surgical procedures, sharp instruments such as scalpels, hypodermic needles and the like can be temporarily inserted into the receiving area, with the sharp portions of these instruments being maintained within the receiving area and out of physical access to operating room personnel.

BRIEF DESCRIPTION OF THE DRAWINGS

While the specification concludes with claims particularly pointing out and distinctly claiming the present invention, it is believed the same will be better understood from the following description taken in conjunction with the accompanying drawings in which:

FIG. 1 is a front elevational view of a disposable receptor for surgical sharps made in accordance with the present invention and illustrated in its normally closed condition;

FIG. 2 is a top plan view of the disposable receptor of FIG. 1; and

FIG. 3 is a partially broken away perspective view of the disposable receptor of FIGS. 1 and 2, illustrated with its top member hingedly rotated to open position.

DETAILED DESCRIPTION OF THE INVENTION

Referring now to the drawings in detail, wherein like numerals indicate the same elements throughout the views, FIGS. 1–3 illustrate a preferred embodiment of the disposable receptor device of the present invention for receiving and retaining sharp implements such as surgical sharps and the like. Particularly, disposable sharps receiving and retaining device 10 is illustrated as comprising a top member 12 connected in spaced apart and substantially parallel relationship with a bottom member 14. Top and bottom members 12 and 14 are respectively connected and spaced from one another by a plurality of peripheral walls (e.g., 16, 18 and 20).

In a preferred embodiment as illustrated in the Figures, a right end peripheral wall 16, oppositely disposed and inwardly facing left end peripheral wall 18, and the longitudinally extending rear peripheral wall 20 provide upstanding peripheral connections between top and bottom members 12 and 14, respectively, to define a substantially enclosed receiving area 22. As will be understood, disposable device 10 may be provided in a variety of shapes and sizes depending upon the particular instruments and/or implements which are to be received and retained. For example, for general applicability in a wide variety of surgical applications, a substantially rectangular conformation is preferred, having a nominal width W of approximately 5" (127 mm), an interior height H of approximately 0.5" (12.7 mm), and a depth D of approximately 1.5" (38.1 mm).

As best illustrated in FIG. 2, top member 12 includes an outer surface 25 which may preferably comprise magnetic features for retaining a plurality of metallic surgical sharps, such as the suture needles 56 illustrated. As also illustrated, outer surface 25 will also preferably include a plurality of distinct regions and/or indicia to facilitate counting and overall accounting of surgical sharps retained thereon. The figures also show an optical upstanding retainer rim 27 which may be slightly inwardly tapered (as best seen in FIG. 2). It is contemplated that retainer rim 27 may be helpful in maintaining randomly placed surgical sharps within the confines of outer surface 25, and may also provide an effective "recessed" arrangement of outer surface 25. Particularly, a peripheral upstanding ridge such as retainer rim 27 might effectively provide a cup-like feature to outer surface 25 wherein suture needles and/or other surgical sharps maintained thereon would be further secluded from inadvertent contact with humans or other structures. A cover or lid (not shown) might also be removably applicable over outer surface to provide further security for post-use disposal procedures.

It is also preferred that at least a portion of top member 12 be hingedly connected to device 10, such as by one or more hinges 29. Particularly, in order to facilitate visual access to the enclosed receiving area 22 therebelow, such a hinged arrangement conveniently enables top member 12 to be articulated from its normally closed position (FIG. 1) to an open position (as seen in FIG. 3) without interfering with the physical retention of any of the surgical sharps held by device 10. The positive retention of surgical sharps deposited upon outer surface 25 by the magnetic features thereof will be sufficient to retain these items while top member 12 is in its open position.

Additionally, it is contemplated that means will be provided for normally maintaining top member 12 in its closed position and to maintain top member 12 in its open position (FIG. 3) until the top member is purposefully articulated back to its closed position. Such means can be conveniently provided in the form of friction-type hinges which resist rotation with a predetermined amount of frictional force. As an alternative, hinges having a plurality of locking positions (e.g., via spring-loaded/detent means) might also be provided with locking positions corresponding to the open and closed positions of top member 12. While a variety of locking mechanisms, hinge arrangements or the like could equally be substituted for the preferred frictional hinge structures, it is preferred that the articulation of top member 12 between closed and open positions, as well as the maintenance of this structure in these positions, be as smooth and uniform as possible. Particularly, snap-type locks or the like should be avoided to minimize the chances of inadvertently liberating a surgical sharp from its retained position on device 10.

As best seen in FIGS. 1 and 3, enclosed receiving area 22 may further preferably be separated into two or more sub-compartments, such as by divider 31. As best shown in FIGS. 1 and 3, receiving area 22 in the illustrated embodiment is divided into left and right portions by divider 31. To the right side of divider 31, a means for releasably receiving and retaining surgical sharps is provided in the form of a plaint material 40 for receiving and retaining hypodermic needles and the like. Pliant material 40 can preferably be provided in the form of a foamed pad (e.g., foamed plastic or polymeric material) into which needles and other surgical sharps can be easily and non-destructively inserted and frictionally retained. As illustrated, two hypodermic needles 54 have been substantially fully inserted into pliant member 40 while a third is partially inserted for illustration purposes. Receiving face 41 of the pliant pad 40 is preferably situated substantially flush with the open edge (e.g., 23) of disposable device 10. It is contemplated that choosing a material for pliant member 40 which is relatively opaque or transparent will further facilitate visual accounting of the number and type of surgical sharps inserted thereinto. While the proximal ends of needles 54 extending outwardly from pad 40 can conveniently be counted, it is also preferred that further visual access be provided by hinged attachment of top member 12, as discussed above, and/or a substantially transparent right end peripheral wall 16. While any pliant material into which surgical sharps can be easily inserted and which features sufficient frictional retention of inserted sharps to prevent inserted sharps from inadvertently removed once inserted, can be utilized for pad 40, it is preferred that a relatively inexpensive and light weight foam material of substantially transparent or opaque color be utilized. Other possible pliant materials might include amorphous and/or gel structures. As is also indicated in FIG. 3, front receiving face 41 may preferably be provided with indicia lines or other means 44 for facilitating the accounting of various surgical sharps inserted thereinto.

The left side of receiving area 22 preferably remains substantially hollow or open to receive and retain additional surgical sharps such as discarded scalpel blades, and/or to temporarily house and protect the "dangerous end" of scalpels (including the blade 50 and handle 52) or hypodermic assemblies. As with outer surface 25 described above, at least a portion of the upper surface 35 of bottom member 14 is provided as a magnetic surface, and can similarly be provided with discrete regions and/or indicia to facilitate accounting procedures. While upper surface 35 may also include a peripheral receiving surface rim 37, it is generally preferred that upper surface 35 will be substantially planar to receive scalpel blades and the like in relatively horizontal position. As seen best in FIGS. 1 and 3, it is preferred that substantially the entire front peripheral edge 23 of disposable device 10 remain substantially open or uncovered in use, so that surgical sharps can be easily inserted into pliant pad 40 and/or inserted and removed from the balance of the covered receiving area 22, as described.

In use, disposable device 10 would be placed in closed condition as seen in FIG. 1 on the upper surface of a surgical instrument table or tray. It is preferred that lower surface 38 of bottom member 14 be provided with one or more attachment means 39 for selectively immovably attaching device 10 to a table top or a tray. For example, attachment means 39 might comprise one or more portions of double-faced tape or the like. The open front edge 23 provides for a preferred single side insertion of the sharp end of surgical instruments, needles, scalpels or the like following use or between uses. While some scalpel blades 50 may be removed from their handles and discarded into receiving area 22 as shown in FIG. 3, scalpels and other sharps which are to be reused during the procedure can be temporarily effectively enclosed within device 10 by insertion into receiving area 22 where they will be held fast against magnetic surface 35 or within foam member 40. Attachment means 39 prevents movement of device 10 upon removal of temporarily stored scalpel.

Hypodermic needles (e.g., 54) and the like can be conveniently inserted into pliant pad 40 and removed from their instruments for safe storage and discarding. Similarly, suture needles or other small metallic surgical sharps can be placed upon magnetic outer surface 25 for similar reliable retention and accounting. The single side insertion enabled at all times, by open front edge 23 is preferred to minimize the potential for inadvertent contact of any retained surgical sharp with personnel in and around the operating field. It is contemplated that one or more of the peripheral walls 16, 18 and 20 can be provided of material which provides significant visual access to the interior of receiving area 22 from outside device 10. For example, one or more of these peripheral walls could be provided in the form of transparent plastic material or the like.

It is also preferred that additional means for providing relatively unencumbered visual access to receiving area 22 be provided. One preferred means for providing additional visual access includes hingedly attaching top member 12 as discussed above. At any time, complete visual access can be gained to the interior of receiving area 22 by simply rotating hinged top member 12 from its closed position to its open position. Simple return of top member 12 to its closed position then enables continued use of the device during surgical procedures and/or convenient disposal. As will be appreciated, open edge 23 continues to provide access to enclosed receiving area 22 at all times, regardless of whether top member 12 is in open or closed position. While an optional lid structure (not shown) might be provided to enclose outer surface 25 and at least part of open edge 23, such lid would not be contemplated for use until the surgical procedure had concluded and all counts were verified.

Having shown and described the preferred embodiments of the present invention, further adaptions of the disposable surgical sharp receiving and retaining device shown and described herein can be accomplished by appropriate modifications by one of ordinary skill in the art without departing from the scope of the present invention. Several of such potential modifications have been mentioned, and others will be apparent to those skilled in the art. For example, the means for providing relatively unencumbered visual access to the interior of the enclosed receiving area of the present invention could alternately be provided in the form of a slidable drawer member or the like. Particularly, receiving area 22 might comprise structure which could be slided outwardly through open edge 23 for visual access without significant movement of either the top or bottom members.

Accordingly, the scope of the present invention should be considered in terms of the following claims, and is understood not to be limited to the details of structure and operation shown and described in the specification and drawings.

We claim:

1. A disposable device for receiving and retaining sharp implements, said device comprising:
    a top member and a bottom member connected in spaced apart relationship by a plurality of adjacent peripheral walls which define a substantially enclosed receiving area therebetween, said top member having an outer magnetic surface, and at least a portion of said receiving area having a magnetic surface adjacent said bottom member;
    an open edge which provides access to said receiving area for insertion and temporary storage of surgical sharps;
    means located at least partially between said top and bottom members for releasably receiving and retaining surgical sharps; and
    means associated with said top member for providing visual access to said receiving area.

2. The disposable device of claim 1, wherein said means for releasably receiving surgical sharps comprises a pliant material for receiving and frictionally holding surgical sharps at least partially inserted thereinto.

3. The disposable device of claim 2, wherein said pliant material comprises foamed material.

4. The disposable device of claim 1, wherein said top member comprises a hinged portion which can be selectively opened to provide visual access to said receiving area.

5. The disposable device of claim 4, wherein said peripheral walls comprise a rear wall and two oppositely disposed end walls located between said top and bottom members, and wherein at least a portion of said top member is hingedly attached to said rear wall for articulation between open and closed positions.

6. The disposable device of claim 4, further comprising means for maintaining said hinged portion of the top member in either an open or closed position relative to said receiving area.

7. The disposable device of claim 6, wherein said means for maintaining said top member in open position comprises a friction hinge joining said hinged portion to said rear wall, said friction hinge providing predetermined resistance to movement of said top member.

8. The disposable device of claim 1, wherein said top member, bottom member and peripheral walls are joined together to provide a substantially hollow box-like structure and defining said open edge providing access to both said receiving area and said releasably receiving means therewithin.

9. A disposable device for receiving and retaining surgical sharps, said device comprising:
    a top member and a bottom member connected in generally parallel, spaced apart relationship by a plurality of adjacent upstanding peripheral walls which define a substantially enclosed receiving area therebetween, said top member having an outer magnetic surface, and at least a portion of said receiving area having a magnetic surface adjacent said bottom member;
    an open edge providing access to said receiving area for insertion and temporary storage of surgical sharps therewithin;
    a foamed member located at least partially between said top and bottom members for receiving and retaining surgical sharps; and
    at least a portion of said top member being hingedly attached to at least one of said peripheral walls to facilitate selective visual access to said receiving area.

10. The disposable device of claim 9, wherein said peripheral walls comprise a rear wall and two oppositely disposed end walls located between said top and bottom members, and wherein at least a portion of said top member is hingedly attached to said rear wall for articulation between open and closed positions.

11. The disposable device of claim 9, further comprising means for maintaining said hinged portion of the top member in either an open or closed position relative to said receiving area.

12. The disposable device of claim 11, wherein said means for maintaining said top member in open position comprises a friction hinge joining said hinged portion to said rear wall, whereby said friction hinge resists movement of said top member once moved to its open position.

13. The disposable device of claim 9, wherein at least one of said peripheral walls is substantially transparent.

14. The disposable device of claim 9, wherein said top member, bottom member and peripheral walls are joined together to provide a substantially hollow box-like structure having a substantially open front peripheral edge which provides relatively unencumbered access to both said receiving area and said frictional receiving means therewithin.

15. The disposable device of claim 9, wherein said top and bottom members are substantially rectangular in conformation, said peripheral walls comprise a substantially rectangular rear wall and a pair of inwardly facing substantially rectangular end walls, and wherein the front peripheral wall is substantially open to enable insertion of surgical sharps into said receiving area and said foamed member from outside of said device.

16. A disposable device for receiving and retaining surgical sharps, said device comprising:

a top member and a bottom member connected in generally aligned, parallel, spaced apart relationship by a plurality of adjacent peripheral walls to define a substantially enclosed receiving area therebetween, said top and bottom members having front and rear edges, said top member also having an outer magnetic surface, and at least a portion of said receiving area comprising a magnetic surface adjacent said bottom member;

an open edge adjacent the front edge of said bottom member providing access to said receiving area;

a foamed member located at least partially between said top and bottom members and within said receiving area for insertably receiving and retaining surgical sharps; and at least a portion of said top member being hingedly attached to at least one of said peripheral walls to facilitate selective visual access to said receiving area.

17. The disposable device of claim 16, wherein said top member is hingedly attached adjacent its rear edge to at least one peripheral wall.

18. The disposable device of claim 16, wherein the peripheral wall between the respective front edges of said top and bottom members in closed position is substantially open to define said open edge and enable relatively unencumbered insertion of surgical sharps into said receiving area and said foamed member from outside the device.

* * * * *